United States Patent
Wu et al.

(10) Patent No.: US 12,358,922 B1
(45) Date of Patent: Jul. 15, 2025

(54) BERBERINE ALPHA-KETOGLUTARATE SALT, CRYSTALLINE FORM, METHODS OF PREPARATION AND APPLICATIONS THEREOF

(71) Applicant: LONGEVITAN BIOSCIENCES LLC, Natick, MA (US)

(72) Inventors: Dedong Wu, Newton, MA (US); Branden Wu, Newton, MA (US); Jacob Dongjian Shi, Boston, MA (US)

(73) Assignee: Longevitan Biosciences LLC, Natick, MA (US)

( * ) Notice: Subject to any disclaimer, the term of this patent is extended or adjusted under 35 U.S.C. 154(b) by 0 days.

(21) Appl. No.: 18/678,224

(22) Filed: May 30, 2024

(51) Int. Cl.
*C07D 491/153* (2006.01)
*A61K 31/4375* (2006.01)
*C07C 55/12* (2006.01)

(52) U.S. Cl.
CPC ...... *C07D 491/153* (2013.01); *A61K 31/4375* (2013.01); *C07C 55/12* (2013.01); *C07B 2200/13* (2013.01)

(58) Field of Classification Search
CPC ... C07D 49/153; C07D 55/12; A61K 31/4375
See application file for complete search history.

(56) References Cited

U.S. PATENT DOCUMENTS 10,577,379 B1  3/2020  Xie et al.
11,345,697 B1  5/2022  Wu et al.

OTHER PUBLICATIONS

Sato, H., et al., "Role of malic acid in solubilizing excess berberine accumulating in vacuoles of Coptis japonica", Phytochemistry 1992, Received in revised fom Feb. 18, 1992, pp. 3451-3454, vol. 31, No. 10.
Wang, C., et al., "Sweet Berberine", Cryst. Growth Des. 2016, Received Oct. 19, 2015, Revised Dec. 3, 2015, Published Dec. 18, 2015, pp. 933-939, 16.

*Primary Examiner* — Kevin E Weddington
(74) *Attorney, Agent, or Firm* — Banner & Witcoff, Ltd.

(57) ABSTRACT

The present disclosure relates to berberine alpha-ketoglutarate salts, which can be used in a pharmaceutical or nutraceutical composition for the treatment or prevention of bacterial infections, cardiovascular diseases, or other conditions. The present disclosure also relates to crystalline forms, methods of preparing berberine alpha-ketoglutarate salts and applications thereof.

15 Claims, 6 Drawing Sheets

BERBERINE ALPHA-KETOGLUTARATE SALT, CRYSTALLINE FORM, METHODS OF PREPARATION AND APPLICATIONS THEREOF

FIELD OF THE DISCLOSURE

The present disclosure relates to berberine alpha-ketoglutarate salts, which can be used in a pharmaceutical and/or nutraceutical composition for the treatment or prevention of bacterial infections, cardiovascular diseases, and/or other conditions. The present disclosure also relates to crystalline forms of the berberine alpha-ketoglutarate salts and methods of preparing them and applications thereof.

BACKGROUND OF THE DISCLOSURE

Berberine (IUPAC name: 5,6-dihydro-9,10-dimethoxybenzo[g]-1,3-benzodioxolo[5,6-a]quinolizinium) is a quaternary benzylisoquinoline alkaloid, which is found in a variety of plants, including barberry, goldenseal, Oregon grapes and coptis. These plants have long been used alone or in combination with other ingredients in traditional medicines, such as Native American and Chinese ones, to treat a wide variety of illnesses, including eye conditions, diarrhea, jaundice, and acne. Recent clinical investigations on some compositions containing berberine have also demonstrated a wide spectrum of pharmacological effects, including antihypertensive, antiarrhythmic, antihyperglycemic, anticancer, antidepressant, anxiolytic, neuroprotective, antioxidant, anti-inflammatory, analgesic, and hypolipidemic activities. For example, berberine has been clinically used as an antibacterial agent for gastrointestinal infections and diarrhea. Berberine has also been used as an active ingredient in various dietary supplements.

The common solid forms of berberine in commercial pharmaceutical and/or nutraceutical products are those of berberine chloride dihydrate. The major disadvantage of using berberine chloride as a dihydrate form is that it could lose more than 8% of the water in an elevated temperature or a low humidity environment. On the one hand, it also could uptake about 8% of water and convert to a tetrahydrate form of berberine chloride in water or a high humidity environment. On the other hand, it could lose some water to a monohydrate form in a dry environment. Thus, there are various challenges to control the solvent residue content in berberine chloride solid forms during manufacture of the drug substance, which significantly impact the quality of the berberine products. The other disadvantage of using berberine chloride dihydrate is that the nearly 10% chloride anion component of it is a potential hazard for patients with Type 2 diabetes.

Therefore, it is desirable to identify an alternative salt of berberine that has improved physicochemical properties for better berberine containing drug substances and drug products and better quality-control during manufacture thereof. It is also beneficial to obtain a chloride-free salt to reduce the potential risk for patients with Type 2 diabetes. Furthermore, it can be advantageous to generate a synergic effect to enhance berberine's clinical and/or nutritional performance by using an organic counterion with extra therapeutic activity.

The particular crystalline form of a drug candidate can have a significant impact on the physicochemical property of a drug substance, for example, crystallinity, thermal stability and hygroscopicity. However, it is very difficult to predict the properties of an optimized crystalline form of the alternative berberine salt with an acceptable chemical purity profile for quality control and a suitable physical property for manufacture of the drug substance and drug product.

BRIEF SUMMARY OF THE DISCLOSURE

In a primary aspect, the present disclosure provides berberine salts and their solid salt forms, including crystalline forms, either alone or as part of a pharmaceutical and/or nutraceutical composition. The present disclosure is also directed to methods of preparation of the berberine salts and their solid salt forms, including crystalline forms, as well as pharmaceutical and/or nutraceutical products containing these salts. The present disclosure more particularly provides a berberine salt of alpha-ketoglutaric acid or alpha-ketoglutarate. The berberine salt of alpha-ketoglutaric acid or alpha-ketoglutarate has herein been found to provide a number of unexpected advantages, including high stability in its anhydrous form, high thermal stability, high aqueous stability, and synergistic effects between the berberine and alpha-ketoglutarate portions of the salt. In another aspect, the present disclosure is directed to methods of treating a subject having a central nervous system disease, cardiovascular disease, infection disease, or other condition (e.g., diabetes) by administering to the subject a pharmaceutically effective amount of the berberine salt.

Alpha-ketoglutaric acid or alpha-ketoglutarate in a salt form, also known as 2-oxoglutaric acid (IUPAC name: 2-oxopentanedioic acid), is an important biological compound. Currently, alpha-ketoglutaric acid (or its alpha-ketoglutarate salt form) is marketed as a food supplement for possibly improving longevity, immune regulation, enzyme cofactor, and other activities. Alpha-ketoglutaric acid is generally well-tolerated and may be taken by mouth or by injection. Moreover, the combination of berberine and alpha-ketoglutaric acid in one salt form has herein been found to provide synergetic effects. In particular embodiments, alpha-ketoglutaric acid is used herein as a counterion to form crystalline salts with the berberine cation. It is an additional objective of this disclosure to provide optimal crystalline forms of berberine alpha-ketoglutarate salts and their preparation methods. It is also an objective of this disclosure to provide pharmaceutical or nutraceutical compositions comprising the berberine alpha-ketoglutarate disclosed herein.

More particularly, provided herein is a berberine alpha-ketoglutarate salt, which can be used in a pharmaceutical or nutraceutical composition for treatment or prevention of diseases or conditions in a human or an animal in need thereof. The berberine alpha-ketoglutarate salt as a solid comprises berberine as a cation and neutralized alpha-ketoglutaric acid (alpha-ketoglutarate) as an anion. Berberine is a molecule (cation) with the following structure.

The alpha-ketoglutarate anion can have two forms, a monoprotonated form and an unprotonated form. The structures of the monoprotonated alpha-ketoglutaric acid and unprotonated (divalent) alpha-ketoglutarate anions are shown below:

In one embodiment, provided herein is a berberine alpha-ketoglutarate salt with a about 1:1 molar ratio (berberine to alpha-ketoglutarate, so called berberine hydrogen alpha-ketoglutarate) or about 2:1 molar ratio (so called berberine hemi-alpha-ketoglutarate), or with about from about 1:1 to about 2:1 molar ratio, preferred 1:1, between the berberine cation and the alpha-ketoglutarate anion. Berberine hydrogen alpha-ketoglutarate and berberine hemi-alpha-ketoglutarate have one of the following chemical structures, respectively:

In another embodiment, provided herein is a berberine hydrogen alpha-ketoglutarate salt, wherein the molar ratio (berberine to alpha-ketoglutarate) is about 1:1; wherein the salt has the following chemical structure.

In one embodiment, provided herein is a crystalline berberine hydrogen alpha-ketoglutarate salt. In one embodiment as disclosed herein, the berberine hydrogen alpha-ketoglutarate salt is a crystalline anhydrous form. In another embodiment as disclosed herein, the crystalline berberine hydrogen alpha-ketoglutarate salt is an anhydrous form and is characterized by a PXRD pattern comprising one or more peaks expressed as 2θ±0.2° of about 7.1°, about 8.4°, about 8.6°, about 14.1°, about 15.5°, about 16.8°, about 19.1°, about 19.5°, about 20.6°, and about 24.7°.

Remarkably, the crystalline form of the exemplary berberine alpha-ketoglutarate disclosed herein demonstrates an optimal physical property as a stable anhydrous form, which benefits quality control, manufacture process and storage condition of drug substances and drug products.

Surprisingly, the crystalline form of the exemplary berberine alpha-ketoglutarate shows a higher aqueous solubility than the commercial berberine hydrochloride, indicating a possible higher in vivo concentration and a better therapeutic activity.

Furthermore, crystalline berberine alpha-ketoglutarate disclosed herein eliminates undesired counter ion, specifically, the chloride anion of berberine chloride usually used in commercially available berberine products, so that reducing some side effects caused by the chloride anion.

In another aspect, provided herein are methods of preparing the desired crystalline berberine hydrogen alpha-ketoglutarate salts comprising mixing a berberine acetone adduct and alpha-ketoglutaric acid.

In one embodiment, the disclosed method comprises mixing a berberine acetone adduct and alpha-ketoglutaric acid in a solvent or solvents.

In one embodiment, the disclosed method comprises preparing a berberine acetone adduct as an intermediate, followed by mixing the berberine acetone adduct and alpha-ketoglutaric acid.

The general reaction disclosed herein to prepare the exemplary crystalline berberine hydrogen alpha-ketoglutarate from berberine chloride is shown as the following scheme:

In another embodiment, the disclosed method comprises mixing berberine hemi-sulfate and alpha-ketoglutaric acid. In one embodiment, the alpha-ketoglutaric acid is neutralized by a base, for example, sodium hydroxide (NaOH) after mixing with berberine hemi-sulfate and precipitating the desired berberine alpha-ketoglutaric salt. The general reaction disclosed herein to prepare the crystalline berberine hydrogen alpha-ketoglutarate from berberine hemi-sulfate is shown as the following scheme:

In another aspect, the disclosure provides a composition of a pharmaceutical or nutraceutical product comprising a berberine alpha-ketoglutarate salt.

In another aspect, the disclosure provides a method for the treatment or prevention of a cardiovascular disease, aging, or other conditions in a human or an animal in need thereof, comprising providing a composition of a pharmaceutical or nutraceutical product comprising a berberine alpha-ketoglutarate salt disclosed herein.

The foregoing summary is illustrative only and is not intended to be in any way limiting. In addition to the illustrative aspects, embodiments, and features described above, further aspects, embodiments, and features will become apparent by reference to the drawings and the following detailed description. Other objects, advantages and features of the present disclosure will become apparent from the following specification taken in conjunction with the accompanying examples and drawings.

DETAILED DESCRIPTION OF THE DISCLOSURE

The present disclosure relates to berberine alpha-ketoglutarate salts, including crystalline forms, which can be used in a pharmaceutical or nutraceutical composition for the treatment or prevention of bacterial infections, cardiovascular diseases, or other conditions in a subject. The present disclosure also relates to crystalline forms of the berberine alpha-ketoglutarate salts, methods of preparing and applications thereof.

The embodiments of this disclosure are not limited to any specific and exemplary compositions and methods disclosed herein, which can vary and are understood by skilled artisans. Unless defined otherwise, all technical and scientific terms used herein have the same meaning as commonly understood by one of ordinary skills in the art to which embodiments of the disclosure pertain. Many methods and materials similar, modified, or equivalent to those described herein can be used in the practice of the embodiments of the present disclosure without undue experimentation, the preferred materials and methods are described herein.

Berberine Alpha-Ketoglutarate Salt

In one aspect, described herein is a berberine alpha-ketoglutarate salt comprising berberine as a cation and an alpha-ketoglutarate anion Berberine is a cationic molecule having the following structure:

The alpha-ketoglutarate anion can have two forms, a monoprotonated form and an unprotonated form.

The monoprotonated alpha-ketoglutarate anion has the following structure:

The unprotonated alpha-ketoglutarate anion (i.e., dianion) has the following structure:

In one embodiment, the berberine alpha-ketoglutarate salt has an approximate or precise 1:1 molar ratio between the cation and the anion, also referred to herein as berberine hydrogen alpha-ketoglutarate.

The berberine hydrogen alpha-ketoglutarate salt has the following chemical structure.

In another embodiment, the berberine alpha-ketoglutarate salt has an approximate or precise 2:1 molar ratio between the cation and the anion, also referred to herein as berberine hemi-alpha-ketoglutarate. The berberine hemi-alpha-ketoglutarate salt has the following chemical structure.

In another embodiment, the berberine alpha-ketoglutarate salt has an approximate or precise molar ratio within a range of 1:1 to about 2:1 between the cation and the anion. In embodiments where the molar ratio is higher than 1:1 but lower than 2:1, the berberine alpha-ketoglutarate salt is typically a mixture of berberine hydrogen alpha-ketoglutarate and berberine hemi-alpha-ketoglutarate. In some embodiments, the berberine alpha-ketoglutarate salt has a molar ratio of the berberine and the alpha-ketoglutarate from precisely or about 0.9:1 to 1:0.9.

Notably, the berberine alpha-ketoglutarate salt, as disclosed herein, is not a simple mixture of a berberine salt and alpha-ketoglutarate salt either in solution or in solid form. In such a simple mixture, the berberine and alpha-ketoglutarate ions are in weak association with each other while also typically being in association with other ions present, such as chloride and sodium. Instead, for purposes of the present invention, the berberine alpha-ketoglutarate salt results from a reaction between berberine and alpha-ketoglutarate ions with the end result of the berberine and alpha-ketoglutarate ions being strongly associated with each other and not associated with other ions. Thus, a "salt", as used herein, is distinct from a physical mixture of the two counterions, in which there is no proton transfer from the anion to the cation. Moreover, the term "salt," as used herein, refers to a solid form. The solid salt form is also composed of only berberine and alpha-ketoglutarate ions, with other anions, such as chloride or sodium, either not present or present in a trace amount (e.g., less than 0.1 or 0.01 wt %).

Nuclear Magnetic Resonance (NMR) spectroscopy is an important analytical technique to confirm the ratio between the berberine cation and the alpha-ketoglutarate anion. Alternatively, or in addition, single crystal x-ray diffraction can also confirm the molar ratio of a salt as well as provide a three-dimensional crystal structure that shows the proton location involved in forming a salt.

In one embodiment, the berberine alpha-ketoglutarate salt disclosed herein is amorphous or partially amorphous. In another embodiment, the berberine alpha-ketoglutarate salt disclosed herein is crystalline or partially crystalline. The crystalline berberine alpha-ketoglutarate salt may be, for example a single crystalline form, polycrystalline, or a mixture of crystalline forms. In another embodiment, the berberine alpha-ketoglutarate salt is of anhydrous form, or is a solvate, hydrate, co-crystal, or a mixture thereof.

As further discussed below, both NMR spectroscopy and single crystal structure analysis of the exemplary berberine hydrogen alpha-ketoglutarate salt confirmed that the ratio between the berberine cation and the alpha-ketoglutarate anion is present in an approximate 1:1 molar ratio. Notably, the single crystal structure also reveals that one of the two carboxyl protons is transferred while the other one stays in the carboxyl group.

In some embodiments, the berberine alpha-ketoglutarate salt is "chemically pure," e.g. contains less than about 1%, about 2%, about 3%, about 4%, about 5%, about 6%, about 7%, about 8%, about 9%, about 10%, about 15%, or about 20% of other chemical substances on a weight basis.

In one embodiment, the berberine alpha-ketoglutarate salt is a "single-component" solid, which may be, for example, an anhydrous salt form and/or a form not containing any additional ionic species. In another embodiment, the berberine alpha-ketoglutarate salt is a "multiple-component" solid comprising one or more additional species, to form a co-crystal and/or a solvate. Nuclear Magnetic Resonance (NMR) spectroscopy and/or thermogravimetric analysis (TGA) are usually used to determine the additional component(s) in a cocrystal or a solvate.

Crystalline Form of Berberine Hydrogen Alpha-Ketoglutarate

The term "solid form", "solid", or related terms, as used herein, refers to a physical form that is not in a liquid or a gaseous state. As mentioned above, a solid form may be crystalline, amorphous, or a mixture thereof.

The term "amorphous," "amorphous form," or related terms refer to a substance, component, or product that is not crystalline as determined by X-ray diffraction, solid NMR, or other analytical techniques as known by one skilled in the art. In particular, the term "amorphous form" describes a disordered solid form, e.g. a solid form lacking long range crystalline order.

The term "crystalline", "crystalline solid", "crystal solid", "crystal form", "crystalline form", or related terms, as used herein, refer to a solid substance, material, compound, a mixture of compounds, or product exhibiting three-dimensional order, which generally exhibit a distinctive PXRD pattern or solid NMR spectrum with sharply defined peaks.

In one aspect, provided herein is a crystalline form of berberine hydrogen alpha-ketoglutarate. The crystalline berberine hydrogen alpha-ketoglutarate, as disclosed herein, comprises berberine as a cation and an alpha-ketoglutaric acid (alpha-ketoglutarate) as an anion. In one embodiment, the salt has a molar ratio of the berberine and the alpha-ketoglutarate of from about 0.9:1 to about 1:0.9. In another embodiment, the salt is a crystalline solid of at least 75% crystalline material.

A crystalline form of salt (or a crystalline salt) can be a material containing a single component or multiple components. The crystalline salt may be or include, for example, a polymorph, a solvate (including hydrate), a cocrystal, a single crystalline form, or a mixture thereof. In some embodiments, as the crystallinity is determined, confirmed, or elucidated by, e.g., by PXRD, solid NMR, Raman spectroscopy, polarized light microscopy (PLM), thermal analysis, and/or moisture absorption analysis. In some embodiments, a crystalline solid comprises about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% crystallinity, or an amount of crystallinity within a range bounded by any two of the foregoing values. In some embodiments, a crystalline solid of a substance may be substantially or completely free of an amorphous form. In some embodiments, a crystalline solid of a substance may be "physically pure," e.g., contains less than about 5%, about 10%, about 15%, about 20%, about 25%, about 30%, about 35%, or about 40% of other crystal forms or amorphous forms on a weight basis.

A crystalline berberine alpha-ketoglutarate salt may or may not be polymorphic. The terms "polymorphs," "polymorphic forms", or related terms refer to a crystalline solid comprising two or more crystal forms of the same molecule, mixtures of molecules, salts, or combination thereof.

The term "anhydrous form" or "neat form" refers to a solid form of a substance which does not contain water molecules or only in a trace amount (e.g., less than 1, 0.1, or 0.01 wt %).

The term "solvate" refers to a berberine alpha-ketoglutarate salt containing one or more solvent molecules. The berberine alpha-ketoglutarate salt may alternatively be unsolvated or desolvated. The term "desolvated" refers to a solid form of a substance that has been removed of solvent molecules.

Powder X-ray diffraction (PXRD) is particularly useful for identifying, analyzing, and/or characterizing crystalline forms. PXRD also provides a fingerprint for each crystalline form with a unique molecular conformation and molecular packing in its crystal lattice. The crystalline salts disclosed herein were characterized by X-ray powder diffraction technique and found to have their unique PXRD patterns, as further discussed below.

The term "powder X-ray diffraction pattern", "X-ray powder diffraction pattern", "PXRD pattern", "XRPD pattern", or "powder X-ray diffraction diagram" refers to the experimentally observed diffractogram or parameters derived therefrom. Powder X-ray diffraction patterns are characterized by peak positions (abscissa) and peak intensities (ordinate). The term "2 theta value" (i.e., "2θ") refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). The reference herein to specific 2θ values for a specific solid form is intended to mean the 2θ values (in degrees) as measured using the X-ray diffraction experimental conditions as described herein.

Figure 1:
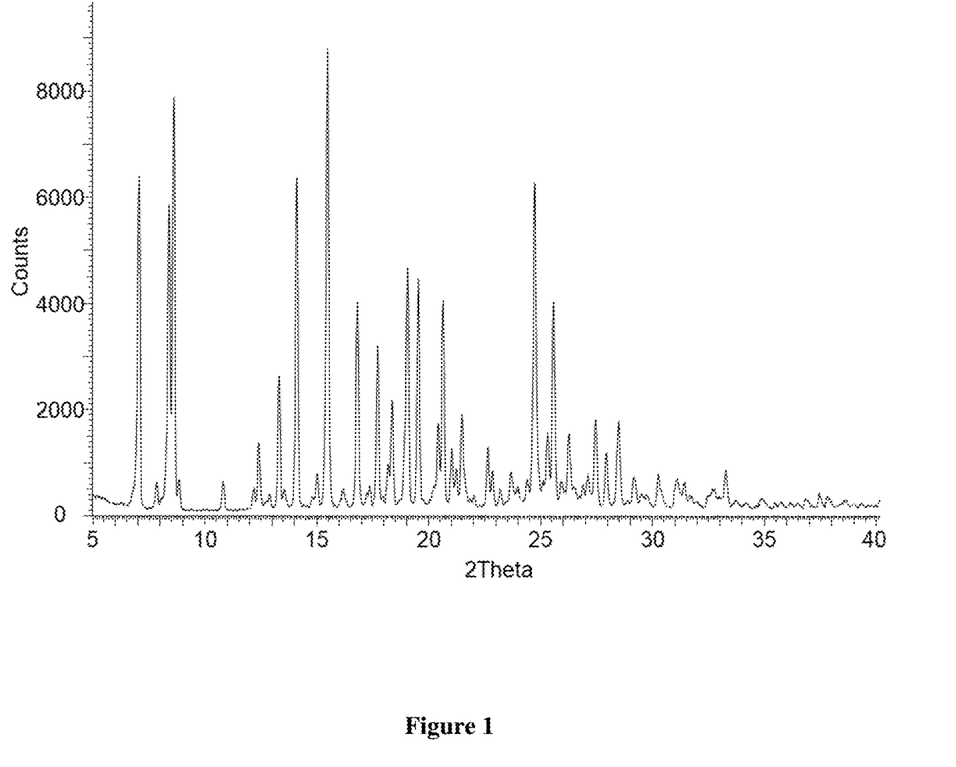
FIG. 1 shows the powder X-ray diffraction pattern of the exemplary crystalline berberine hydrogen alpha-ketoglutarate.

In one embodiment, the crystalline berberine hydrogen alpha-ketoglutarate is an anhydrous form and is characterized by a PXRD pattern comprising one or more peaks expressed as 2θ±0.2° of about 7.1°, about 8.4°, about 8.6°, about 14.1°, about 15.5°, about 16.8°, about 19.1°, about 19.5°, about 20.6°, and about 24.7°. The PXRD pattern of the exemplary crystalline berberine hydrogen alpha-ketoglutarate is shown in FIG. 1.

Figure 2:
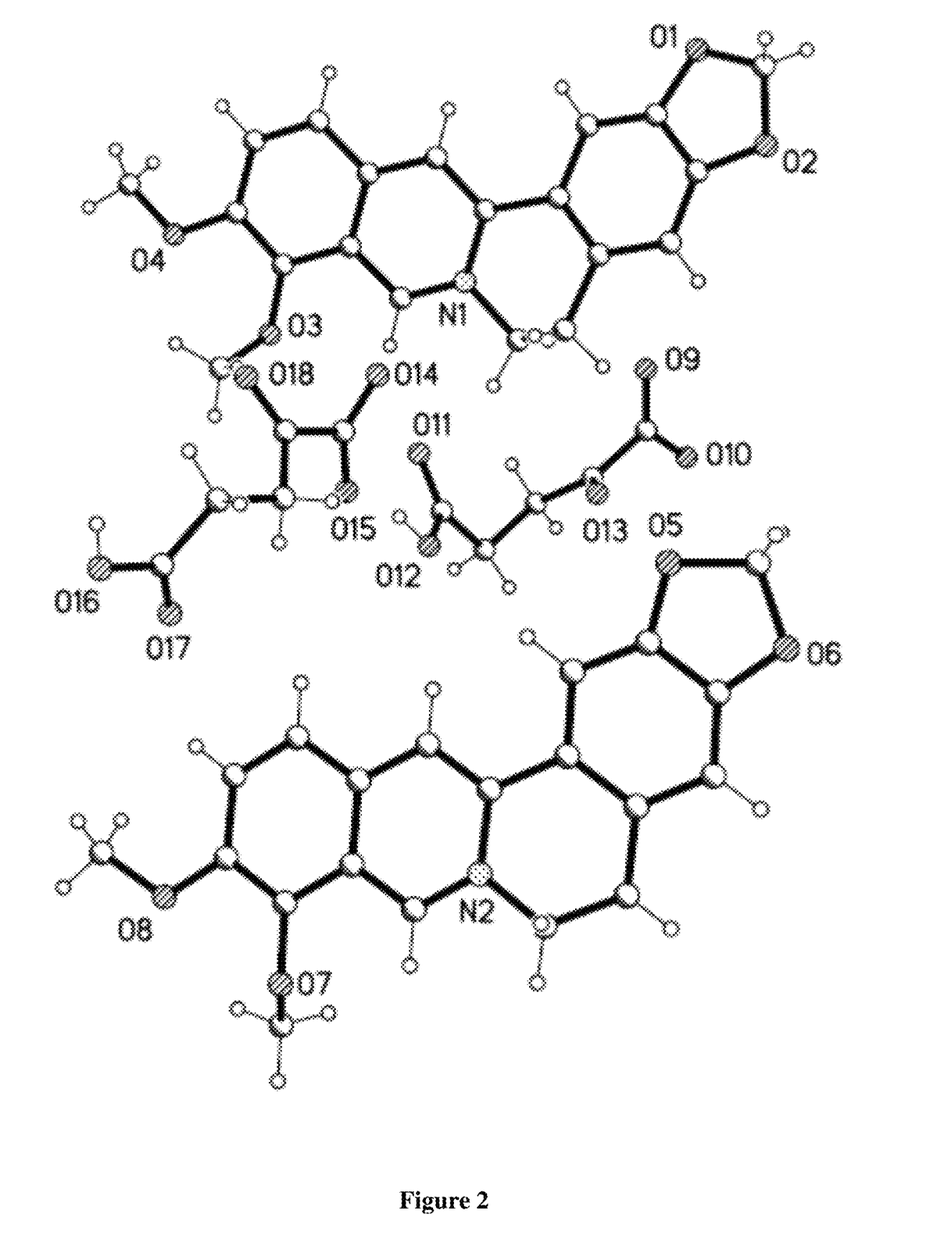
FIG. 2 shows the single crystal structure of the exemplary berberine hydrogen alpha-ketoglutarate.
Figure 3:
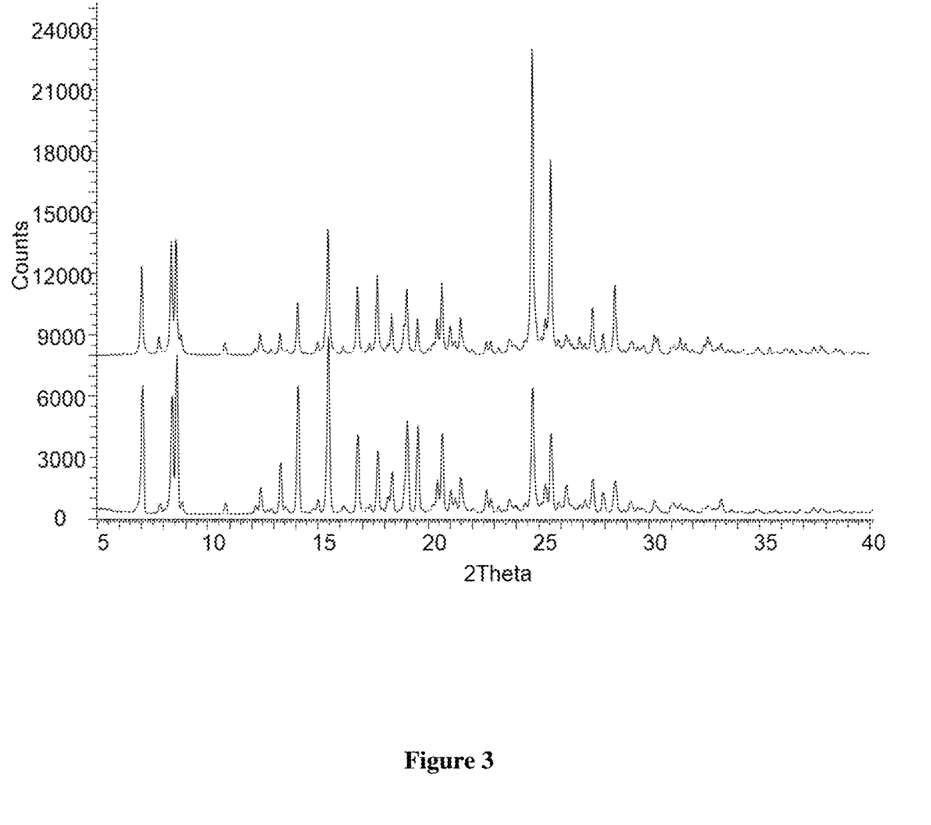
FIG. 3 shows an overlay of the calculated PXRD pattern from single crystal structure with the experimental PXRD pattern of the exemplary crystalline berberine hydrogen alpha-ketoglutarate.

The single crystal structure of the exemplary berberine hydrogen alpha-ketoglutarate has been determined to have the following crystallographic data: triclinic P-1 space group, Z'=2, unit cell dimensions: a=11.7475(5) Å, b=14.2681(6) Å, c=15.2790(6) Å, α=101.394(1)°, β=102.756(1)°, γ=112.146(1)° and V=2198.9(2) Å$^3$. As shown in the crystal in FIG. 2, two berberine cations and two alpha-ketoglutarate anions co-exist in the asymmetric unit, confirming a 1:1 molar ratio between the two ions. The locations of the hydrogen atoms in the crystal structure also demonstrated a hydrogen alpha-ketoglutarate with only one of the two protons being transferred. As shown in FIG. 3, the overlay of the simulated PXRD pattern with the experimental confirms that the single crystal used for crystal structure determination represents the crystals in the bulk material of the exemplary crystalline berberine hydrogen alpha-ketoglutarate.

Remarkably, the exemplary crystalline form of berberine hydrogen alpha-ketoglutarate disclosed herein as a stable anhydrous form possesses optimal physical properties. These properties are beneficial for improving quality control, simplifying the manufacturing process, and improving storage stability of the crystalline form.

Figure 4:
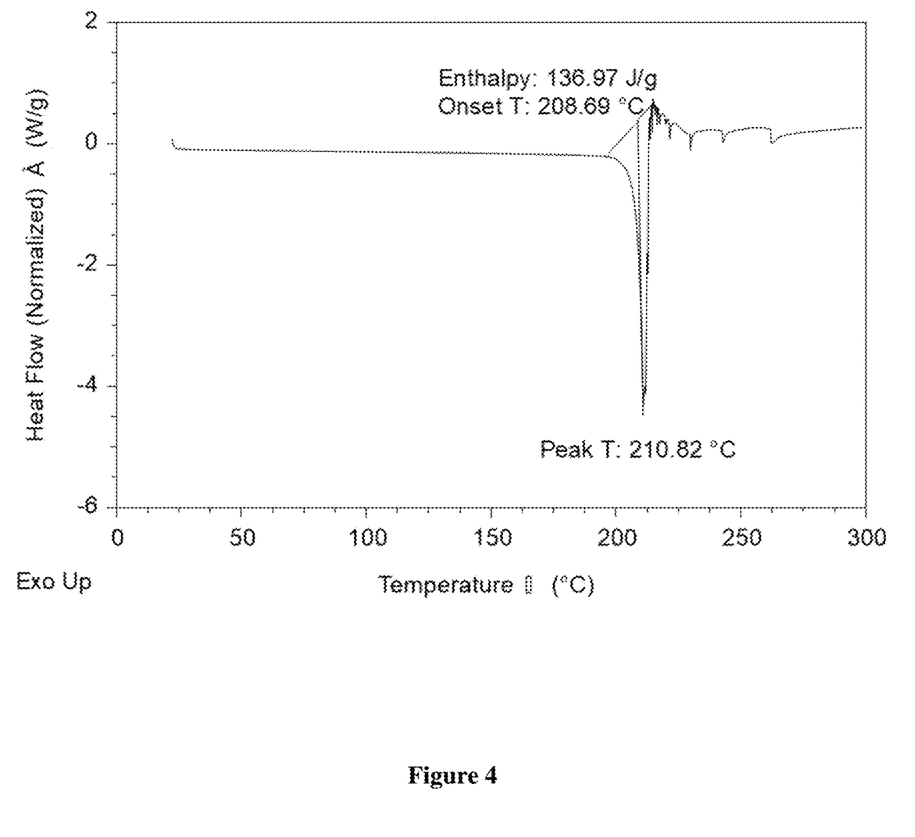
FIG. 4 shows the DSC diagram of the exemplary crystalline berberine hydrogen alpha-ketoglutarate.
Figure 5:
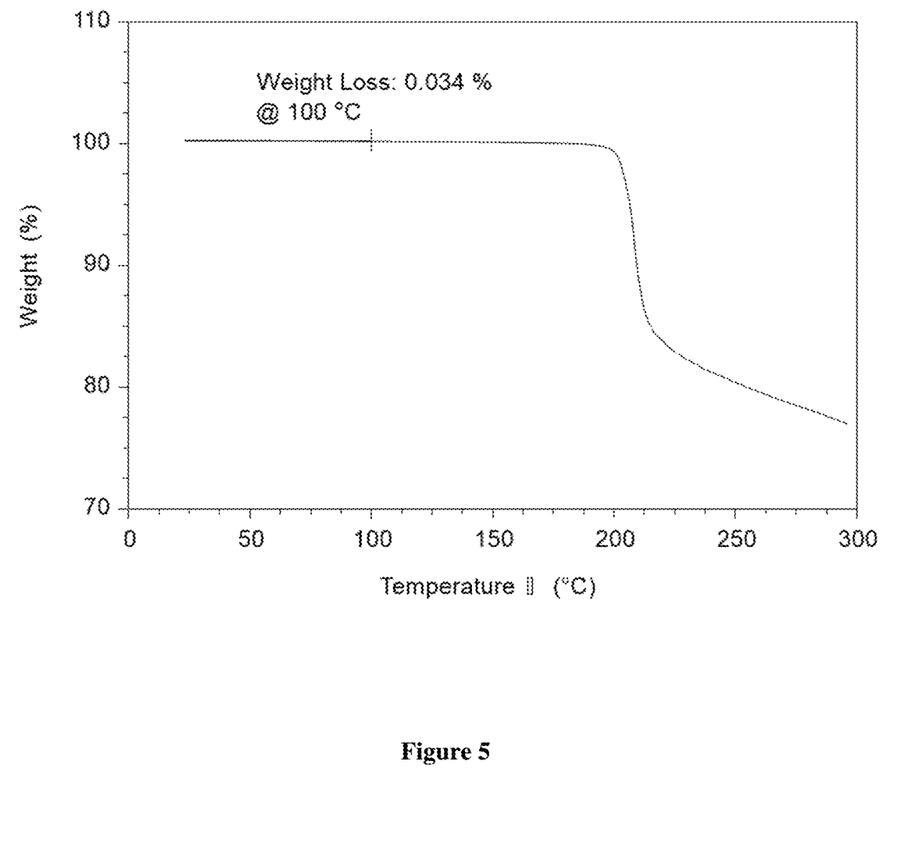
FIG. 5 shows the TGA diagram of the exemplary crystalline berberine hydrogen alpha-ketoglutarate.

Various stable anhydrous crystalline forms of berberine hydrogen alpha-ketoglutarate were obtained from different reaction conditions as disclosed herein. The exemplary crystalline berberine hydrogen alpha-ketoglutarate demonstrated an optimal physical property, including thermal stability. As shown in FIG. 4 and FIG. 5, there was no significant weight loss or any thermal events for the exemplary berberine hydrogen alpha-ketoglutarate even when it was heated to about 200° C. in thermal analysis experiments. The crystalline berberine alpha-ketoglutarate started to melt and/or decompose only at above 208° C. Anhydrous crystalline forms of the berberine hydrogen alpha-ketoglutarate disclosed herein also demonstrated a non-hygroscopic property in a high humidity environment, without a form change even when stirring in an aqueous suspension. The thermal stability and non-hygroscopicity of crystalline berberine hydrogen alpha-ketoglutarates would improve quality control, the manufacturing process, and storage stability of the crystalline of the anhydrous crystalline form.

Surprisingly, the exemplary crystalline berberine hydrogen alpha-ketoglutarate disclosed herein exhibited at least five times higher aqueous solubility than that of the commercial berberine hydrochloride (see Example 3). 10 mg of crystalline berberine hydrogen alpha-ketoglutarate was dissolved in 2.0 ml of water to yield a clear yellow solution, while 10 mg of berberine chloride was suspended in 10 ml of water and remained as a yellow suspension after stirring at the room temperature for about 1 day. Significantly, the better aqueous solubility of crystalline berberine hydrogen alpha-ketoglutarate salts indicate a possible higher in vivo concentration, which could result in better therapeutic activities.

Method of Preparing Crystalline Berberine Hydrogen Alpha-ketoglutarate

It is important to develop a robust process method to prepare berberine salts. In some embodiments, the berberine salt was prepared by an anion exchange process starting with berberine chloride. After being dissolved in water, berberine chloride reacted with alternative acids in their neutralized forms, usually the sodium or potassium salt, and then cooled down to precipitate the desire alternative salts (e.g., Wang, et al. Cryst. Growth Des. 2016, 16(2), 933-939; Xie, et al. U.S. Pat. No. 10,577,379, March 2020). These methods have the advantage of directly precipitating the desired berberine salt without isolating any berberine intermediate. However, such a method is limited to preparation of organic salts of berberine whose aqueous solubility is low enough to allow it to precipitate out from reaction mixtures. By applying such a method to prepare the berberine alpha-ketoglutarate salts disclosed herein, only berberine chloride precipitated out from the reaction mixture.

With berberine chloride as the starting material, a two-step reaction process was herein employed. In the two-step process, a berberine acetone adduct was used as an intermediate to avoid the solubility obstacle of berberine chloride. The berberine acetone adduct was prepared as an intermediate according to a procedure disclosed in U.S. Pat. No. 11,345,697). As disclosed herein, the exemplary crystalline berberine hydrogen alpha-ketoglutarate salt has been successfully obtained herein by reaction between the berberine acetone adduct and alpha-ketoglutaric acid with simultaneous or subsequent crystallization (i.e., "reaction crystallization").

In another aspect, provided herein are methods to prepare the desired crystalline berberine hydrogen alpha-ketoglutarate salts, comprising mixing a berberine acetone adduct and alpha-ketoglutaric acid. In one embodiment, the method comprises mixing a berberine acetone adduct and alpha-ketoglutaric acid to form a reaction mixture. In another embodiment, the method comprises mixing a berberine acetone adduct and alpha-ketoglutaric acid in a solvent to form a reaction mixture. In another embodiment, the method comprises mixing a berberine acetone adduct and alpha-ketoglutaric acid for reaction crystallization.

In one embodiment, the method of preparation comprises mixing a berberine acetone adduct and alpha-ketoglutaric acid, wherein the berberine acetone adduct is derived from berberine chloride. The general reaction disclosed herein to prepare crystalline berberine hydrogen alpha-ketoglutarate salts from berberine chloride is shown in the following scheme:

In another embodiment, the disclosed method comprises mixing a berberine acetone adduct and alpha-ketoglutaric acid under conditions suited for reaction crystallization, wherein the berberine acetone adduct results from a reaction between berberine chloride and acetone.

Reaction crystallization (or reactive crystallization or crystallization reaction) refers to a phenomenon comprising simultaneous reaction, mass transfer, crystal nucleation and growth, as well as possible secondary processes of aging, ripening, agglomeration, and breakage. Reaction crystallization has herein been used in the preparation of crystalline berberine alpha-ketoglutarate from a reaction mixture of one of a berberine ketone adduct and alpha-ketoglutaric acid as disclosed herein. Surprisingly, the resulting crystalline berberine hydrogen alpha-ketoglutarates produced by this method have a high level of crystallinity and a high chemical purity profile.

To produce a high quality crystalline berberine hydrogen alpha-ketoglutarate salt from the reaction mixture, various factors, including type of solvent, reaction temperature, reaction time and the starting material for the berberine ketone adduct, were considered in an effort to achieve a robust reaction crystallization process.

In one embodiment, the disclosed method comprises mixing a berberine acetone adduct and alpha-ketoglutaric acid, wherein the berberine ketone adduct and the alpha-ketoglutaric acid have a molar ratio between about 1:1 and about 2:1, preferably about 1:1. When about 2:1 molar ratio between the berberine ketone adduct and alpha-ketoglutaric acid was employed in the disclosed methods, an exemplary crystalline intermediate, presumed to be a berberine hemi-alpha-ketoglutarate salt, was observed by PXRD analysis. However, the crystalline intermediate converted to the crystalline berberine hydrogen alpha-ketoglutarate in the same reaction mixture. In a particular embodiment, the method to prepare a berberine hydrogen alpha-ketoglutarate salt comprises mixing a berberine acetone adduct and alpha-ketoglutaric acid, wherein the berberine ketone adduct and alpha-ketoglutaric acid have about 1:1 molar ratio.

The term "solvent," as used herein, refers to any inorganic or organic solvent. Certain solvents can be a part of the crystalline salt disclosed herein. Solvents are useful in the disclosed method or article, product, or composition as a reaction solvent or carrier solvent. Suitable solvents include, but are not limited to, lower alkyl alcohols, aliphatic and aromatic hydrocarbons, dialkyl ethers, dialkyl ketones, alkyl acetates, acetonitrile, chlorinated alkanes, dimethyl sulfoxide (DMSO), dimethylformamide (DMF), and aqueous solvents. More specific examples of solvents include, but are not limited to, methanol, ethanol, propanol, isopropanol and butanol, isobutanol, ethyl acetate, iso-propyl acetate, n-heptane, diethyl ether, tert-butyl methyl ether, acetone, dichloromethane, and water. The solvents used herein can be a single solvent or a mixture of one or more solvents. Crystalline berberine hydrogen alpha-ketoglutarate salts were prepared by reaction crystallization with selection of reaction different solvents. The solvents used in reaction crystallization to crystallize the anhydrous crystalline form of berberine hydrogen alpha-ketoglutarate were typically selected from water, ethanol, isopropanol, acetonitrile, tetrahydrofuran, or ethyl acetate, preferably ethanol, or a mixture of any two or more of these solvents.

In one embodiment, the disclosed method comprises mixing a berberine acetone adduct and alpha-ketoglutaric acid in a solvent. In another embodiment, the disclosed method comprises mixing a berberine acetone adduct and alpha-ketoglutaric acid in a solvent to form a reaction mixture. In another embodiment, the disclosed method comprises mixing a berberine acetone adduct and alpha-ketoglutaric acid in water, ethanol, isopropanol, acetonitrile, tetrahydrofuran, ethanol, or a combination thereof. In another embodiment, the disclosed method comprises mixing a berberine acetone adduct and alpha-ketoglutaric acid in ethanol.

Reaction crystallization temperatures and times were also optimized. At room temperature (typically, about 18-27° C., or about 25° C.) or a lower temperature, the reaction does not proceed. Only at an elevated temperature, typically above 60° C., the reaction starts to proceed and precipitate the desired crystalline berberine hydrogen alpha-ketoglutarate salts. On the other hand, if the reaction temperature is too high and/or the reaction time at the elevated temperature is too long, the crystalline salt starts to decompose and generates chemical impurities. The preferred reaction time is about 0.5-2 hours with a reaction temperature of 60-80° C., followed by stirring at the room temperature for 1-2 hours for crystalline berberine alpha-ketoglutarate to be completely precipitated out from the reaction mixture.

In one embodiment, the disclosed method comprises mixing a berberine acetone adduct and alpha-ketoglutaric acid in a solvent to form a reaction mixture, wherein the reaction mixture is kept at a temperature of about 60 to 80° C. In one embodiment, the temperature of the reaction mixture is from about 60 to 80° C. for about 0.5 to about 2 hours. In another embodiment, the temperature of the reaction mixture is kept at about 60 to 80° C. for about 0.5 to about 2 hours, then kept at a room temperature for about 1 to 2 hours. In another embodiment, the disclosed method further comprises stirring the reaction mixture for additional time of from about 1 to 2 hours at room temperature.

As disclosed herein, berberine hemi-sulfate (or berberine sulfate) was also employed to prepare crystalline berberine hydrogen alpha-ketoglutarate using a one-step reaction process. Although less commonly used as a starting material compared to berberine chloride, berberine sulfate provides much higher aqueous solubility compared to berberine chloride and this can advantageously permit directly precipitating the desired crystalline berberine hydrogen alpha-ketoglutarate salts without the need to isolate a berberine intermediate.

In another aspect, provided herein are methods to prepare the desired crystalline berberine hydrogen alpha-ketoglutarate salts from berberine hemi-sulfate salt comprising neutralizing a mixture solution of berberine hemi-sulfate and alpha-ketoglutaric acid with a base at a room temperature. In one embodiment, the base is sodium hydroxide. In another embodiment, the solvent is ethanol, water, or a combination thereof. The general reaction scheme disclosed herein to prepare the crystalline berberine hydrogen alpha-ketoglutarate salts disclosed herein from a berberine hemi-sulfate is shown in the following scheme:

As an example for the methods disclosed herein, berberine hemi-sulfate and alpha-ketoglutaric acid (about 1:1 molar ratio) were dissolved in a minimum amount of water to yield a solution. The solution was then neutralized with a NaOH aqueous solution. The crystalline berberine hydrogen alpha-ketoglutarate salts precipitated from the reaction mixture. Additional anti-solvent, e.g. ethanol, isopropanol, acetone, tetrahydrofuran, or acetonitrile, may be added into the aqueous suspension to improve the yield of the berberine product.

Pharmaceutical Compositions

In an aspect, disclosed herein is a composition comprising a berberine alpha-ketoglutarate salt as disclosed herein. In one embodiment, the composition further comprises a pharmaceutical or nutraceutical acceptable carrier. In another embodiment, the composition comprises an effective amount or a therapeutically effective amount of the berberine alpha-ketoglutarate salt as disclosed herein, to treat, improve, inhibit, or ameliorate a condition or a symptom of a disorder of a subject, in a clinically relevant manner.

As one skilled in the art will ascertain, an effective amount or an amount sufficient to treat (e.g. therapeutically effective amount) refers to the amount of a pharmaceutical or nutraceutical composition administered to improve, inhibit, or ameliorate a condition of a subject, or a symptom of a disorder, in a clinically relevant manner. The subject refers to a human or animal. Any improvement in the subject is considered sufficient to achieve the treatment. Preferably, an amount sufficient to treat is an amount that prevents the occurrence or one or more symptoms of the diseases or conditions or is an amount that reduces the severity of, or the length of time during which a subject suffers from, one or more symptoms of the diseases or conditions.

By its "pharmaceutical composition", the berberine alpha-ketoglutarate salts as disclosed herein provide the therapeutically or biologically active agent for formulation into a suitable delivery means for administration to a subject. For the purposes of this disclosure, pharmaceutical compositions suitable for delivering the berberine alpha-ketoglutarate salts as disclosed herein can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of the aforementioned formulations can be prepared by well-known and accepted methods of art.

In one embodiment, the pharmaceutical compositions disclosed herein comprise a berberine alpha-ketoglutarate as disclosed herein and a pharmaceutically acceptable carrier or excipient. The term "pharmaceutically acceptable" means approved by a regulatory agency of the Federal or a state government or listed in the U.S. Pharmacopeia or other generally recognized pharmacopeia for use in animals, and more particularly in humans.

Examples of suitable pharmaceutically acceptable carriers or excipients that can be used in said pharmaceutical compositions include, but are not limited to, sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, phosphate buffer solutions, lubricants, coloring agents, releasing agents, coating agents, sweetening, flavoring or perfuming agents, preservatives, or antioxidants.

The term "excipient" refers to additives and stabilizers typically employed in the art (all of which are termed "excipients"), including for example, buffering agents, stabilizing agents, preservatives, isotonifiers, non-ionic detergents, antioxidants and/or other miscellaneous additives.

Stabilizers refer to a broad category of excipients which can range in function from a bulking agent to an additive which solubilizes the disclosed salts or helps to prevent denaturation of the same. Additional conventional excipients include, for example, fillers (e.g., starch), chelating agents (e.g., EDTA), antioxidants (e.g., alpha-ketoglutaric acid, methionine, vitamin E) and cosolvents.

The term "carrier" refers to a diluent, adjuvant, excipient, or vehicle with which the pharmaceutical composition is administered. Such pharmaceutical carriers are illustratively sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions are optionally employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, also contains wetting or emulsifying agents, or pH buffering agents. These compositions optionally take the form of solutions, suspensions, emulsion, tablets, pills, capsules, powders, sustained release formulations and the like. The composition is optionally formulated as a suppository, with traditional binders and carriers such as triglycerides. Oral formulation illustratively includes standard carriers such as pharmaceutical grades of mannitol, lactose, starch, magnesium stearate, sodium saccharine, cellulose, magnesium carbonate, etc.

In one embodiment, the pharmaceutical compositions disclosed herein are formulated to release the composition immediately upon administration (e.g., targeted delivery) or at any predetermined time period after administration using controlled or extended-release formulations. Administration of the pharmaceutical composition in controlled or extended release formulations is useful where the composition, either alone or in combination, has (i) a narrow therapeutic index; (ii) a narrow absorption window in the gastro-intestinal tract; or (iii) a short biological half-life, so that frequent dosing during a day is required in order to sustain a therapeutic level. One skilled in the art will ascertain compositions for controlled or extended release of the pharmaceutical composition. In an aspect, controlled release can be obtained by controlled release compositions and coatings which are known to those of skill in the art.

Methods of Use/Treatment

The berberine alpha-ketoglutarate salts disclosed herein can be employed in methods of therapeutic or prophylactic treatment of a subject. In the method, a subject is administered a therapeutically effective amount of the berberine salt, such as any of those described above, to treat or prevent a condition or disease. The subject is typically a human but may be an animal in some cases. In some embodiments, the method is for treating or preventing gastrointestinal infections or other conditions. The condition or disease being treated may be any disease state or condition that can be treated or prevented by administering a berberine salt, either alone or in combination with another medication.

By "treating" is meant administering a berberine alpha-ketoglutarate salt as disclosed herein for prophylactic and/or therapeutic purposes. Prophylactic treatment may be administered, for example, to a subject who is not yet ill, but who is susceptible to, or otherwise at risk of, a particular disorder. In some embodiments, the disorder is a gastrointestinal infection or a related condition. In other embodiments, the treatment treats an existing cardiovascular disease or condition or reduces the likelihood of a subject developing a cardiovascular disease or condition. In other embodiments, the method of treatment treats a central nervous system disease, infection, or any other condition that can be treated by administering a berberine salt. The method of treatment may also be used for slowing the aging process, maintaining a more youthful appearance, or maintaining a higher level of energy. Therapeutic treatment may be administered to, for example, a subject already suffering from a disorder to improve or stabilize the subject's condition. Thus, in the claims and embodiments described herein, treating is the administration to a subject either for therapeutic or prophylactic purposes.

In another aspect, disclosed herein is a method comprising providing a berberine alpha-ketoglutarate salt disclosed herein to a subject for therapeutic or prophylactic treatment of the subject.

The methods of treatment disclosed herein may be performed alone or in conjunction with another medical or pharmaceutical treatment. The methods of treatment may further be combined with other therapeutic agents, including for example, another antibacterial agent.

The foregoing detailed description is illustrative only and is not intended to be in any way limiting. In addition to the illustrative aspects, embodiments, and features described above, further aspects, embodiments, and features will become apparent by reference to the drawings and the following detailed description.

All publications, patent applications, issued patents, and other documents referred to in this specification are indicative of the level of ordinary skill in the art to which this disclosure pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present disclosure is further illustrated by the following examples, which should not be considered as limiting in any way.

EXAMPLES

Embodiments of the present disclosure are further defined in the following non-limiting Examples. These Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Analytical Methods

Nuclear Magnetic Resonance (NMR) Spectroscopy

In general, the structures of end-products of the salt were confirmed by nuclear magnetic resonance (NMR) spectroscopy. Proton magnetic resonance spectra were taken using a Bruker Advance 500 (500 MHz) and NMR chemical shift values were given in ppm. Proton NMR measurements were taken at ambient temperature unless otherwise specified; the following abbreviations have been used for characterizing NMR peaks: s, singlet; d, doublet; t, triplet; q, quartet; m, multiplet; dd, doublet of doublets; ddd, doublet of doublet of doublet; dt, doublet of triplets; bs, broad signal. The chemical shifts (δ) of the NMR peak are reported in parts per million (ppm) downfield of tetramethylsilane (TMS) and referenced to the respective residual un-deuterated solvent peak as follows: MeOH-$d_4$=3.31 ppm for $^1$H-NMR. Apparent coupling constants (J) are reported in Hz.

Powder X-Ray Diffraction (PXRD) Analysis

In general, the crystalline forms of the salts were analyzed by powder X-ray diffraction (PXRD), which provides a fingerprint of a crystalline form. PXRD analysis was performed using a Bruker D8 diffractometer by Bruker AXS Inc™ (Madison, Wisconsin). The PXRD spectra were obtained by mounting a sample (approximately 10 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (e.g., about 1.54 angstroms). The sample was exposed for 1 second per 0.02 degree 2-theta increment (continuous scan mode) over the range 5 degrees to 40 degrees 2-theta in theta-theta mode. The running time was ~15 min for such a measurement.

PXRD 2θ values may vary with a reasonable range, e.g., in the range ±0.2° and the PXRD intensities may vary when measured for essentially the same crystalline form for a variety of reasons including, for example, preferred orientation.

Differential Scanning Calorimetry (DSC) Analysis

DSC analysis was performed on samples prepared according to standard methods using a Q SERIES™ Q1000 DSC calorimeter available from TA INSTRUMENTS® (New Castle, Delaware). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C./minute. Thermal data was analyzed using standard software, e.g., Universal Analysis v.4.5A from TA INSTRUMENTS®.

Thermogravimetry Analysis (TGA)

TGA was performed on samples prepared according to standard methods using a Q SERIES™ Q5000 thermogravimetry analyzer available from TA Instruments INSTRUMENTS® (New Castle, Delaware). A sample (approximately 5 mg) was placed into an aluminum sample pan and transferred to the TGA furnace. The instrument was purged with nitrogen at 50 mL/min and data collected between 25° C. and 300° C., using a dynamic heating rate of 10° C./minute. Thermal data was analyzed using standard software, e.g., Universal Analysis v.4.5A from TA INSTRUMENTS®.

Example 1

Preparation of Berberine Alpha-Ketoglutarate from Berberine Chloride

Step A. Preparation of the Intermediate of Berberine Acetone Adduct.

6.112 g of berberine chloride dihydrate (15.0 mmol) was suspended in 150 ml of MeOH and stirred at the room temperature for about 15 minutes until a homogeneous yellow slurry was obtained. To the suspension, 31.0 ml of 0.50 N NaOH aqueous solution was added, a dark orange-brown solution was obtained. The solution was filtered immediately, and a yellow solid started to precipitate after 30.0 ml of acetone was added. 50.0 ml of water was added to the suspension, and the yellow suspension was stirred at room temperature for about 1 hour to yield a homogenous slurry. The yellow solid was collected by filtration, washed with small amount of water, and then dried in air for 2 hours. 3.902 g of crystalline berberine acetone adduct was obtained. About additional 50 ml of water was added to the light brown filtrate solution, and more yellow solid precipitated. Extra 0.990 g of crystalline berberine acetone solid was collected after filtered, washed, and dried. (Total yield: 82.9%)

Step B. Reaction Crystallization 3.932 g of crystalline berberine acetone adduct (10.0 mmol) and 1.461 mg of white alpha-ketoglutaric acid (10.0 mmol) was mixed in 50 ml of EtOH. The suspension was heated to 75° C. and stirred for 1 hour. The homogenous slurry of yellow solid in brown solution was stirred at room temperature for another 1 hour. The yellow solid was filtered and dried in vacuum for 2 hours. 3.850 g of yellow solid of crystalline berberine hydrogen alpha-ketoglutarate salt was obtained. (Yield: 80.0%)

The proton NMR spectrum of crystalline berberine hydrogen alpha-ketoglutarate was measured in $CD_3OD$, indicating an about 1:1 ratio of the berberine and the alpha-ketoglutarate in the crystalline hydrogen alpha-ketoglutarate. $^1$H NMR (500 MHz, METHANOL-$d_4$) δ ppm 2.5 (t, J=6.8 Hz, 2H) 3.0 (br t, J=6.7 Hz, 2H) 3.2-3.3 (m, 2H) 4.1 (s, 3H) 4.2 (s, 3H) 4.9 (s, 2H) 4.9 (t, J=6.3 Hz, 2H) 6.1 (s, 2H) 6.9 (s, 1H) 7.6 (s, 1H) 8.0 (d, J=9.0 Hz, 1H) 8.1 (d, J=9.0 Hz, 1H) 8.7 (s, 1H) 9.8 (s, 1H).

Crystalline berberine hydrogen alpha-ketoglutarate was analyzed by PXRD. The top ten strongest peaks from the PXRD pattern are tabulated in Table 1 and the PXRD pattern is shown in FIG. 1.

TABLE 1

PXRD Peaks for Berberine Hydrogen Alpha-ketoglutarate

| Angle (2θ ± 0.2°) | Intensity (%) |
|---|---|
| 15.5 | 100.0 |
| 8.6 | 89.1 |
| 14.1 | 72.4 |
| 7.1 | 71.8 |
| 24.7 | 70.6 |
| 8.4 | 67.0 |
| 19.1 | 52.2 |
| 19.5 | 48.8 |
| 20.6 | 44.5 |
| 16.8 | 44.3 |

Single crystals of crystalline berberine alpha-ketoglutarate were obtained by slow evaporation of the solution of ethanol, or ethanol/water. Single crystal analysis of berberine alpha-ketoglutarate confirms a 1:1 molar ratio of berberine cation and hydrogen alpha-ketoglutarate anion. The single crystal structure is shown in FIG. 2. Crystallographic data: triclinic P-1 space group, Z'=2, unit cell dimensions: a=11.7475(5) Å, b=14.2681(6) Å, c=15.2790(6) Å, α=101.394(1)°, β=102.756(1)°, γ=112.146(1)° and V=2198.9(2) Å$^3$. The overlay of the simulated PXRD pattern calculated from the single crystal structure with the experimental PXRD pattern from the bulk material of crystalline berberine alpha-ketoglutarate is shown in FIG. 3.

Crystalline berberine alpha-ketoglutarate was also analyzed by thermal analysis techniques. DSC analysis indicates that the crystalline salt has an endotherm event of melting and decomposition with an onset at about 209° C. and a peak at about 211° C., as shown in FIG. 4. TGA indicates that the crystalline salt exhibits a mass loss of less than 0.1% upon heating from about 25° C. to about 100° C., as shown in FIG. 5.

Example 2

Preparation of Berberine Alpha-ketoglutarate from Berberine Sulphate 384 mg of berberine hemi-sulphate (1.0 mmol) and 146 mg of white alpha-ketoglutaric acid (1.0 mmol) were dissolved in 10.0 ml of water to get a brown solution. The solution was then filtered. To the solution, 1.05 ml of 1.0 N NaOH aqueous solution was added, the solution became darker. 5 mg of crystalline berberine hydrogen alpha-ketoglutarate seeding crystals were added to the solution, and the yellow solid started to precipitate. A homogenous yellow slurry was obtained after stirring at room temperature for about 2 hours. 297 mg of yellow solid of crystalline berberine hydrogen alpha-ketoglutarate was collected after filtered and dried in air. (Yield: 61.7%)

Example 3

Solubility Measurement of Some Berberine Salts 10 mg of crystalline berberine hydrogen alpha-ketoglutarate (from Example 1) was suspended in 2.0 ml of water. A clear yellow solution was obtained after stirring at room temperature for about 1 day. The solubility of crystalline berberine hydrogen alpha-ketoglutarate in water at the room temperature (about 22° C.) is about 5.0 g/L.

10 mg of crystalline berberine chloride dihydrate (from Sigma-Aldrich) was suspended in 10 ml of water. The yellow solid incompletely dissolved, and a yellow solution with small amount of yellow solid was obtained after stirring at room temperature for about 1 day. The solubility of berberine chloride in water at the room temperature (about 20° C.) is about 1.0 g/L (Literature value: "The aqueous solubility of berberine chloride at 25° C. was determined to be 1.96±0.11 mg/mL" from AAPS PharmSciTech, 2010, 11(3), 1466-1475). 10 mg of crystalline berberine hemi-sulfate (from Sigma-Aldrich) was dissolved immediately in about 0.5 ml of water at room temperature. The solubility of berberine hemi-sulfate in water at room temperature (about 20° C.) is larger than 20 g/L.

Example 4

Figure 6:
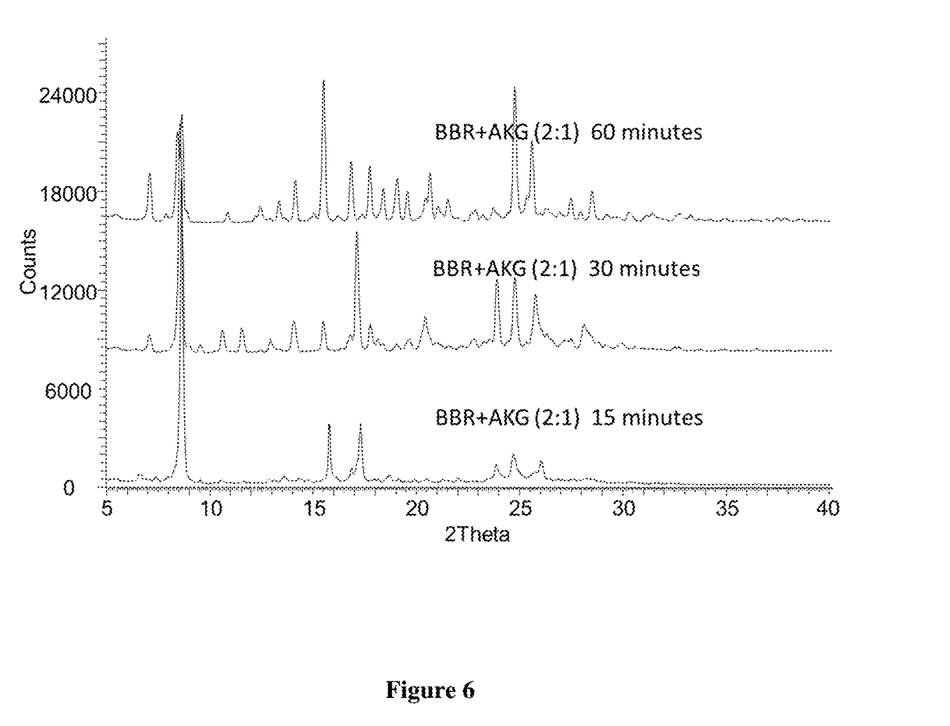
FIG. 6 shows an overlay of patterns from reaction of berberine acetone adduct and alpha-ketoglutaric acid with 2:1 molar ratio.

Preparation of Berberine Alpha-Ketoglutarate with a 2:1 Molar Ratio 79 mg of crystalline berberine acetone adduct (0.20 mmol) and 15 mg of white alpha-ketoglutaric acid (0.10 mmol) was mixed in 0.50 ml of EtOH. The suspension was heated and stirred at 75° C. A small amount of the suspension containing about 2-5 mg of the yellow solid was placed on the PXRD sample holder at about 15-minute, 30-minute, and 60-minute for PXRD measurement. The overlay of PXRD is shown in FIG. 6. After 2 hours, the homogenous slurry was cooled down to room temperature. 25 mg of yellow solid of crystalline berberine hydrogen alpha-ketoglutarate was collected after filtered and dried in air.

What is claimed is:

1. A berberine alpha-ketoglutarate salt in solid form having any one of the following chemical formulas:

2. The berberine alpha-ketoglutarate salt according to claim 1, wherein the salt is amorphous, crystalline, or a mixture thereof.

3. The berberine alpha-ketoglutarate salt according to claim 1, wherein the salt is an anhydrous form, solvate, hydrate, co-crystal, or a mixture thereof.

4. The berberine alpha-ketoglutarate salt according to claim 1, wherein the salt is a single crystalline form.

5. The berberine alpha-ketoglutarate salt according to claim 1, wherein the salt has a molar ratio of the berberine and the neutralized alpha-ketoglutaric acid from about 0.9:1 to about 1:0.9.

6. The berberine hydrogen alpha-ketoglutarate salt according to claim 5, wherein the salt is a crystalline solid.

7. The crystalline berberine hydrogen alpha-ketoglutarate salt according to claim 5, wherein the crystalline solid is an anhydrous form.

8. The crystalline form of berberine hydrogen alpha-ketoglutarate according to claim 5, wherein the salt is an anhydrous form and is characterized by an PXRD pattern comprising one or more peaks expressed as 2θ±0.2° of about 7.1°, about 8.4°, about 8.6°, about 14.1°, about 15.5°, about 16.8°, about 19.1°, about 19.5°, about 20.6°, and about 24.7°.

9. A composition comprising a berberine alpha-ketoglutarate salt according to claim 1 and a pharmaceutically acceptable carrier.

10. The composition according to claim 9, wherein the carrier is a diluent, adjuvant, excipient, vehicle, or mixture thereof.

11. The composition according to claim 9, wherein the composition is formulated into tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols.

12. The composition according to claim 9, wherein the composition is an immediate release composition or extended-release composition.

13. A single crystalline form of a berberine alpha-ketoglutarate salt that exhibits the following PXRD characteristics: triclinic P-1 space group, Z'=2, unit cell dimensions: a=11.7475(5) Å, b=14.2681(6) Å, c=15.2790(6) Å, $\alpha$=101.394(1)°, $\beta$=102.756(1)°, $\gamma$=112.146(1)° and V=2198.9(2) Å$^3$.

14. A method of preparing berberine hydrogen alpha-ketoglutarate according to claim 1 comprises mixing a berberine acetone adduct and alpha-ketoglutaric acid at a temperature of from about 60 to about 80° C.

15. A method of preparing berberine hydrogen alpha-ketoglutarate according to claim 1 from berberine hemi-sulfate by using a direct ion-exchange process comprising neutralizing a mixture solution of berberine hemi-sulfate and alpha-ketoglutaric acid with a base at a room temperature.

\* \* \* \* \*